Aug. 29, 1950 E. S. BOERNER Plant Pat. 975
ROSE PLANT
Filed Sept. 19, 1949
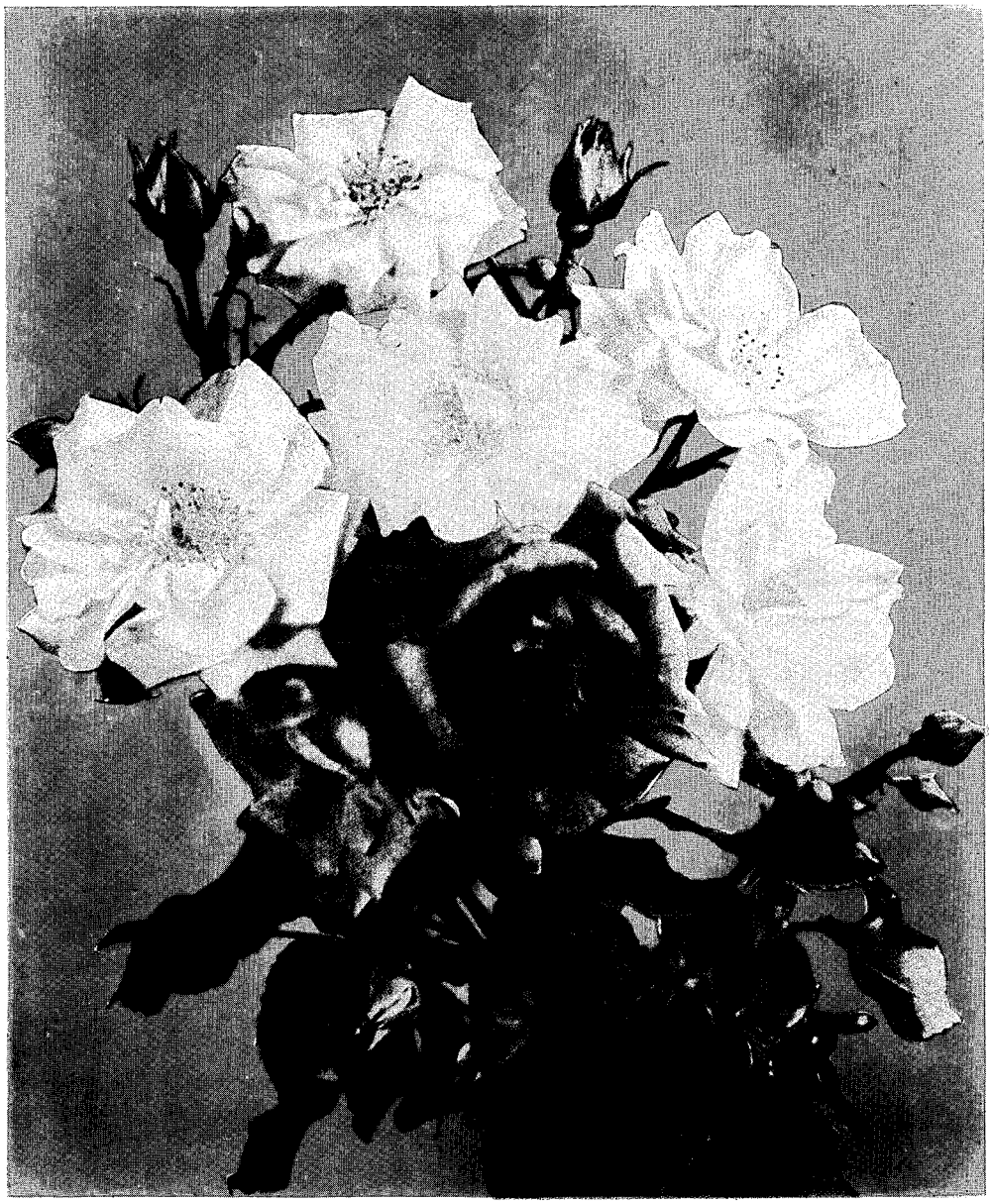
Inventor
E. S. Boerner
By Robert Robb
Attorney Patented Aug. 29, 1950

Plant Pat. 975

UNITED STATES PATENT OFFICE

975

ROSE PLANT

Eugene S. Boerner, Newark, N. Y., assignor to Jackson & Perkins Company, Newark, N. Y., a corporation of New York Application September 19, 1949, Serial No. 116,577

1 Claim. (Cl. 47—61)

The present invention relates to a new and distinct variety of large flowered polyantha rose plant of the floribunda class, resulting from crossing a "Goldilocks" rose and a rose of the "Holiday" variety.

This new variety is unique because of its interesting habit of flowering, speaking with reference to the fact that the flowers change quickly from one color in the bud stage to another color as it opens, then to a still different color when open, and finally finishing of another color. There is no accounting for this mutation, so far as the recent forebears of this variety are concerned and certainly not as regards the immediate parents.

Since the flowers grow in clusters and the flowers of each cluster develop at different times, the interesting phenomenon of color change continues for a long period of time, and since all the colors appear at once to the viewer as a combination it is difficult to believe that this array of contrasting blooms could exist on one and the same bush of this variety.

In general color terminology, each bud is golden yellow, the center bud of each cluster opening first and becoming rose-pink as the petals unfurl. Gradually the rose-pink deepens until the color becomes deep red. While the first bud in any cluster is passing through these stages, other buds are gradually developing, each to move through the same color sequence—yellow to lemon to pink to red.

I was led to make the cross above referred to for the purpose of improving some of the characteristics of the two-tone variety "Holiday," employing to this end, one of the best known new yellow roses "Goldilocks" as the seed parent. This cross did result in an improved rose but also produced the complete mutation of color characteristics having no relation or similarity to those of the antecedents of this new variety, as before premised.

Another very desirable characteristic of this new variety is the lasting quality of the original flowers which hang on, without imparting a detrimental appearance, for several days.

Among other important characteristics of this new variety of plant may be included its vigorous growth and habit of producing many flowers, in clusters (25 to 30 buds), much above the average floribunda known to the trade.

Asexual reproduction of this new variety shows the foregoing characteristics come true to form and are established.

The accompanying drawing illustrates specimens of this new variety showing the flowers at their different stages of development from bud to fully open bloom and the color mutation at the respective stages through which each bud moves.

This new variety was asexually reproduced at Newark, New York, by budding.

The following is a detailed description of the new variety, reference to color being in accordance with Ridgway's Color Standards and Nomenclature:

Parentage: Seedling.

*Seed parent.*—"Goldilocks" (Pl. Pat. #672).

*Pollen parent.*—"Holiday" (unpatented).

Classification:

*Botanic.*—Large flowered polyantha.

*Commercial.*—Floribunda.

*Flower*

(Observations made at Newark, New York, in the month of July in the morning.)

Blooming habit: Recurrent—continuous.

Bud:

*Size.*—Medium.

*Form.*—Ovoid. Is not affected by wet weather.

*Color.*—When sepals first divide—Pomegranate Purple, Plate 12. When petals begin to unfurl—Rose Red, Plate 12. When half blown—inside of petal—Apricot Yellow, Plate 4, center overcast with Tyrian Rose, Plate 12, and outer edges Tyrian Rose, Plate 12; reverse of petals—Pinard Yellow, Plate 4, center with an overcast of Begonia Rose, Plate 1, and outer edges of petals Begonia Rose, Plate 1.

*Sepals.*—Slightly branched; curl back when petals begin to unfurl. Color—outside—Absinthe Green, Plate 31, overlaid with Bordeaux, Plate 12; center vein Bordeaux, Plate 12; inside—Pale Yellow Green, Plate 6.

*Calyx.*—Shape—apple. Size—small. Aspect—smooth. Odor when rubbed—none. Color—Absinthe Green, Plate 31.

*Peduncle.*—Length—medium. Aspect—prickly. Color—Jade Green, Plate 31, with some touches of Auburn, Plate 2. Strength—erect; slender.

*Opening.*—Opens up well. Is not affected by adverse weather conditions.

Bloom:

*Size.*—Medium. Average size when fully expanded, 2½ inches.

*Borne.*—In irregular clusters.

*Stems.*—Medium length; strong.

*Form, when first open.*—Flat. Permanence—Retains its form to the end.

*Petalage.*—Double (full but open center). Number of petals under normal conditions, 20.

*Color.*—*Early stage*—center of flower—Empire Yellow, Plate 4; outer petals—Empire Yellow, Plate 4, with slight touches of Begonia Rose, Plate 1; base of petal (aiglet)—Lemon Chrome, Plate 4; inside of petals—Pinard Yellow, Plate 4, with slight touches of Begonia Rose, Plate 1; reverse of petals—Empire Yellow, Plate 4, except outer row which shows blotches of Begonia Rose, Plate 1, on alternate petals. General tonality from a distance—yellow. *Second stage*—center of flower—Rose Color, Plate 12; outer petals—Rose Color, Plate 12, with lighter edges toward Deep Rose Pink, Plate 12; base—Marguerite Yellow, Plate 30; inside of petals—Rose Color, Plate 12, with lighter edges toward Deep Rose Pink, Plate 12; reverse of petals—lower part of petal Marguerite Yellow, Plate 30. Upper part of petal Deep Rose Pink, Plate 12. General tonality from a distance—pink and yellow. *Final stage*—center of flower—Pomegranate Purple, Plate 12; outer petals—Pomegranate Purple, Plate 12; base—Pale Green Yellow, Plate 5; inside of petals—Pomegranate Purple, Plate 12; reverse of petals—Marguerite Yellow, Plate 30—upper part overcast with Deep Rose Pink, Plate 12. General tonality from a distance—yellow, pink, and red combined.

*Discoloration.*—General tonality at end of first day—Empire Yellow, Plate 4, Rose Color, Plate 12, Pomegranate Purple, Plate 12. Second day—Empire Yellow, Plate 4, Pomegranate Purple, Plate 12. Third day—Pomegranate Purple, Plate 12. As these flowers fade, the fading is only in the part of the petal exposed to the sunlight and immediately beneath these petals or the next petals the Pomegranate Purple, Plate 12, does not appear in the later stages.

Petals:

*Texture.*—Leathery. Is not affected by wet or hot weather.

*Appearance.*—Inside—shiny; outside—satiny.

*Form.*—Oval.

*Arrangement.*—Imbricated (regularly arranged shingle-like). Petaloids in center—none.

*Persistence.*—Drop off cleanly.

*Fragrance.*—Slight. Nature—fruity (Russet apple).

*Lasting quality.*—On the plant and as cut flower—long.

Genital organs:

*Stamens, anthers.*—Medium size; many. Color—Orange Rufous, Plate 2. Arrangement—regular around styles.

*Stamens, filaments (threads).*—Long. Color—Lemon Chrome, Plate 4.

*Pollen.*—Color—Pinard Yellow, Plate 4.

*Styles.*—Columnar; uneven length; medium long; thin.

*Stigmas.*—Color—Picric Yellow, Plate 4.

*Ovaries.*—All enclosed in calyx.

*Plant*

Form: Bush.

Growth: Vigorous; branching.

Foliage: 5 to 7 leaflets.

*Size.*—Medium.

*Quantity.*—Normal.

*Color.*—New foliage: upper side—Oil Green, Plate 5; edges Carmine, Plate 1; under side—Yellowish Oil Green, Plate 5, overcast with Carmine, Plate 1. Old foliage: upper side—Dark Cress Green, Plate 31; under side—Light Cress Green, Plate 31.

*Shape.*—Oval pointed.

*Texture.*—Upper side—leathery; under side—smooth. Ribs and veins—prominent.

*Edge.*—Serrated (saw toothed).

*Serration.*—Single; small.

*Leaf stem.*—Color—Biscay Green, Plate 17. Under side—prickles.

*Stipules.*—Medium length; smooth.

*Disease resistance.*—Resistant.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity—on main stalks from base and on laterals from stalk—ordinary. Form—narrow base; medium length; straight. Color when young—Old Rose, Plate 13. Position—irregular.

*Prickles and hairs.*—None.

I claim:

A new and distinct variety of rose plant of the large flowered polyantha class, characterized as to novelty by its habit of producing flowers, each of which passes through a sequence of color tones as the flowers develop from the bud stage to the full blown bloom; by its vigorous habit of growth and production of numerous flowers in clusters much above the average floribunda and the progressive development of the buds in a cluster, thereby presenting a multi-color display of flowers in each of the respective clusters at one and the same time; and by the lasting quality of each of the flowers, substantially as shown and described.

EUGENE S. BOERNER.

No references cited.